United States Patent
Harris et al.

(10) Patent No.: US 10,736,702 B2
(45) Date of Patent: Aug. 11, 2020

(54) ACTIVATING AND ROTATING SURGICAL END EFFECTORS

(71) Applicant: Ethicon Endo-Surgery, LLC, Guaynabo, PR (US)

(72) Inventors: Jason L. Harris, Lebanon, OH (US); Michael J. Vendely, Lebanon, OH (US); Frederick E. Shelton, IV, Hillsboro, OH (US); Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 494 days.

(21) Appl. No.: 15/238,269

(22) Filed: Aug. 16, 2016

(65) Prior Publication Data

US 2018/0049827 A1 Feb. 22, 2018

(51) Int. Cl.
*A61B 34/35* (2016.01)
*A61B 34/00* (2016.01)
*A61B 46/10* (2016.01)
*A61B 17/29* (2006.01)
(Continued)

(52) U.S. Cl.
CPC .............. *A61B 34/35* (2016.02); *A61B 34/71* (2016.02); *A61B 34/74* (2016.02); *A61B 46/10* (2016.02); *A61B 2017/00477* (2013.01); *A61B 2017/2903* (2013.01); *A61B 2017/2927* (2013.01);
(Continued)

(58) Field of Classification Search
CPC ... A61B 34/35; A61B 34/71; A61B 2034/305; A61B 17/07207; A61B 2017/2903; A61B 46/10; A61B 34/74; A61B 2017/00477; A61B 2017/2927; A61B 2034/742; A61B 2034/741
See application file for complete search history.

(56) References Cited

U.S. PATENT DOCUMENTS

| | | | | |
|---|---|---|---|---|
| 5,855,583 A | * | 1/1999 | Wang | A61B 17/11 318/568.11 |
| 6,394,998 B1 | * | 5/2002 | Wallace | A61B 34/71 606/1 |

(Continued)

OTHER PUBLICATIONS

U.S. Appl. No. 15/131,963 entitled "Method for Operating a Surgical Instrument" filed Apr. 18, 2016.
(Continued)

*Primary Examiner* — Thanh K Truong
*Assistant Examiner* — Katie L Gerth
(74) *Attorney, Agent, or Firm* — Mintz Levin Cohn Ferris Glovsky and Popeo, P.C.

(57) ABSTRACT

Various surgical tools are provided with multi-axis articulation joints and with the ability to rotate distal to the joint. In one embodiment, a surgical tool is provided having an elongate shaft with an end effector disposed at a distal end of the elongate shaft. The end effector can have first and second jaws configured to grasp tissue and a sled or cutting element configured to advance through the jaws and cut tissue therein. A multi-axis articulation joint can be formed on the shaft or between the shaft and the end effector. The joint can allow articulation of the end effector in multiple directions. The end effector can be configured to rotate distal to the multi-axis articulation joint about a longitudinal axis of the elongate shaft. Methods for allowing rotation and articulation of the end effector are also provided.

19 Claims, 9 Drawing Sheets

(51) Int. Cl.
*A61B 34/30* (2016.01)
*A61B 17/00* (2006.01)

(52) U.S. Cl.
CPC ... *A61B 2034/305* (2016.02); *A61B 2034/741* (2016.02); *A61B 2034/742* (2016.02)

(56) References Cited

U.S. PATENT DOCUMENTS

| | | | | |
|---|---|---|---|---|
| 8,931,682 | B2* | 1/2015 | Timm | A61B 17/072 227/178.1 |
| 8,945,098 | B2 | 2/2015 | Seibold et al. | |
| 8,960,519 | B2* | 2/2015 | Whitman | A61B 17/00234 227/175.1 |
| 9,295,522 | B2* | 3/2016 | Kostrzewski | A61B 17/07207 |
| 9,743,995 | B2* | 8/2017 | Lohmeier | A61B 34/71 |
| 2003/0065358 | A1* | 4/2003 | Frecker | A61B 17/29 606/205 |
| 2007/0023477 | A1* | 2/2007 | Whitman | A61B 17/07207 227/175.1 |
| 2007/0106317 | A1* | 5/2007 | Shelton, IV | A61B 17/07207 606/170 |
| 2007/0221701 | A1* | 9/2007 | Ortiz | A61B 17/068 227/175.1 |
| 2009/0171159 | A1* | 7/2009 | Jorgensen | A61B 1/05 600/139 |
| 2009/0188965 | A1* | 7/2009 | Levin | A61B 17/064 227/179.1 |
| 2011/0118708 | A1* | 5/2011 | Burbank | A61B 34/30 606/1 |
| 2011/0118709 | A1 | 5/2011 | Burbank | |
| 2011/0118778 | A1 | 5/2011 | Burbank | |
| 2011/0290856 | A1* | 12/2011 | Shelton, IV | A61B 34/71 227/180.1 |
| 2012/0199632 | A1* | 8/2012 | Spivey | A61B 34/71 227/176.1 |
| 2012/0273546 | A1* | 11/2012 | Whitman | A61B 17/07207 227/175.1 |
| 2013/0153625 | A1* | 6/2013 | Felder | A61B 17/072 227/175.1 |
| 2013/0274722 | A1* | 10/2013 | Kostrzewski | A61B 17/29 606/1 |
| 2013/0282052 | A1 | 10/2013 | Aranyi et al. | |
| 2013/0334281 | A1* | 12/2013 | Williams | A61B 17/068 227/176.1 |
| 2014/0005718 | A1 | 1/2014 | Shelton, IV et al. | |
| 2014/0097227 | A1* | 4/2014 | Aronhalt | A61B 17/0644 227/180.1 |
| 2014/0166727 | A1* | 6/2014 | Swayze | A61B 17/1155 227/179.1 |
| 2014/0276720 | A1* | 9/2014 | Parihar | A61B 17/07207 606/33 |
| 2014/0305991 | A1* | 10/2014 | Parihar | A61B 17/072 227/176.1 |
| 2015/0048141 | A1* | 2/2015 | Felder | A61B 17/11 227/179.1 |
| 2015/0230796 | A1* | 8/2015 | Calderoni | A61B 17/07207 227/175.2 |
| 2016/0095596 | A1* | 4/2016 | Scirica | A61B 17/07207 227/175.1 |
| 2016/0183960 | A1* | 6/2016 | Stroup | A61B 17/29 606/205 |
| 2016/0270779 | A1* | 9/2016 | Chaghaerdi | A61B 34/70 |

OTHER PUBLICATIONS

U.S. Appl. No. 15/177,430 entitled "Surgical Instrument With User Adaptable Techniques" filed Jun. 9, 2016.

* cited by examiner

ACTIVATING AND ROTATING SURGICAL END EFFECTORS

FIELD OF THE INVENTION

Methods and devices are provided for robotic surgery, and in particular for communicating with and controlling robotic tools including actuation and rotation of end effectors.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge.

To ensure proper placement of an end effector and proper tissue engagement, rotation and/or articulation of the end effective is desirable. Some end effectors utilize rotation of an end effector and others utilize multi-axis articulation of an end effector. It is beneficial to be able to use rotation and articulation, but it can be difficult to implement both movements in one end effector, especially with activation shafts that are offset from a central longitudinal axis.

While significant advances have been made in the field of robotic surgery, there remains a need for improved methods, systems, and devices for use in robotic surgery.

SUMMARY OF THE INVENTION

Methods and devices are provided for robotic surgery, and in particular for communicating with and controlling robotic tools including end effectors.

In one aspect, a surgical tool is provided and includes an elongate shaft, and an end effector coupled to a distal end of the elongate shaft. The end effector includes first and second jaws movable between an open position in which the first and second jaws are spaced apart from one another, and a closed position in which the first and second jaws are configured to engage tissue therebetween. The device also includes a joint coupled between the elongate shaft and the end effector. The joint is configured to allow multi-axis articulation of the end effector relative to the elongate shaft. A plurality of articulation members extend distally through the elongate shaft, and at least one of the plurality of articulation members is offset from a central longitudinal axis of the elongate shaft. At least one actuation member extends distally through the elongate shaft. The at least one actuation member is operatively connected to the end effector such that rotation of the at least one actuation member is configured to move the first and second jaws between the open and closed positions.

The surgical tool can have a variety of configurations. In one embodiment, the at least one actuation member includes at least one flexible torque transmission tube that extends through a center of the joint. The device can also include a rotary actuation cable coupled to the end effector such that rotation of the second rotary actuation cable is configured to advance a cutting element through the end effector. In certain aspects, the plurality of articulation members are configured to translate longitudinally along the elongate shaft to articulate the end effector. The plurality of articulation members can include, for example, a first articulation cable, a second articulation cable, and an articulation tube. In other aspects, the device can include a rotation actuator extending through the elongate shaft and operatively connected to the joint such that rotation of the rotation actuator causes rotation of the joint and corresponding rotation of the end effector relative to the elongate shaft. In another embodiment, a proximal end of the elongate shaft is coupled to a housing that is configured to couple to a plurality of motors on a tool driver of a surgical system. In yet another embodiment, each actuation member includes a proximal gear positioned proximal of the joint, and a distal gear positioned distal of the joint, the proximal and distal gears being configured to translate a rotational force from the at least one actuation member across the joint.

A robotic tool is also provided and in one embodiment the tool includes a housing having a plurality of gear assemblies, each gear assembly being configured to couple to a motor on a tool driver of a surgical robot. The tool further includes an elongate shaft extending distally from the housing. An end effector having first and second jaws is pivotably coupled to a distal end of the elongate shaft. The end effector is rotatable about a longitudinal axis thereof. The tool also includes a multi-axis articulation joint coupled between the elongate shaft and the end effector and configured to allow multi-axis articulation of the end effector, and a plurality of rotatory drive actuators extending through the elongate shaft and configured to actuate at least closing of the first and second jaws.

In one embodiment, the plurality of rotatory drive actuators comprise non-concentric actuators. At least one of the plurality of rotatory drive actuators can include a flexible torque transmission tubing extending through a center of the articulation joint. For example, the plurality of rotatory drive actuators can include a first flexible torque transmission tubing and a second flexible torque transmission tubing concentric with one another and extending through a center of the articulation joint. In other aspects, the tool can include a sled disposed within the end effector and configured to advance distally through at least one of the first and second jaws to eject at least one staple into tissue engaged between the first and second jaws, wherein at least one of the plurality of rotatory drive actuators is configured to actuate advancement of the sled. In another embodiment, the plurality of rotatory drive actuators can include a first flexible torque transmission tubing and a second flexible torque transmission tubing concentric with one another and extending through a center of the articulation joint, the first flexible torque transmission tubing being configured to actuate closing of the first and second jaws, the second flexible torque transmission tubing being configured to actuate advancement of the sled. In other embodiments, the tool can include a first articulation cable, a second articulation cable, and an articulation tube that extend distally through the elongate shaft and that are coupled to the articulation joint.

Various surgical methods are also provided and in one embodiment the method includes actuating a motor on a tool driver of a surgical robot to cause an actuation shaft extending through a shaft of a tool coupled to the tool driver to rotate and thereby cause opposed jaws on an end effector of the tool to close, the actuation shaft extending offset from a central longitudinal axis of the shaft, and the rotary force being transferred across an articulation joint that allows multi-axial articulation of the end effector. The method further includes actuating a motor on the tool driver to rotate a rotation actuation shaft extending through the shaft of the tool to thereby cause rotation of the end effector relative to the shaft and distal of the articulation joint. The method can also include actuating a motor on the tool driver to articulate at least one articulation member extending through the shaft of the tool, which thereby causes articulation of the end effector relative to the shaft. The method can also include actuating a motor on the tool driver to cause a second actuation shaft extending through the shaft to rotate and thereby cause a cutting element disposed within the opposed jaws to advance to cut tissue grasped between the opposed jaws, the actuation shaft extending offset from the central longitudinal axis of the shaft. In other embodiments, the method can include actuating a motor on the tool driver to cause at least one articulation cable to translate longitudinally along the shaft and thereby cause the end effector to articulate about the articulation joint.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
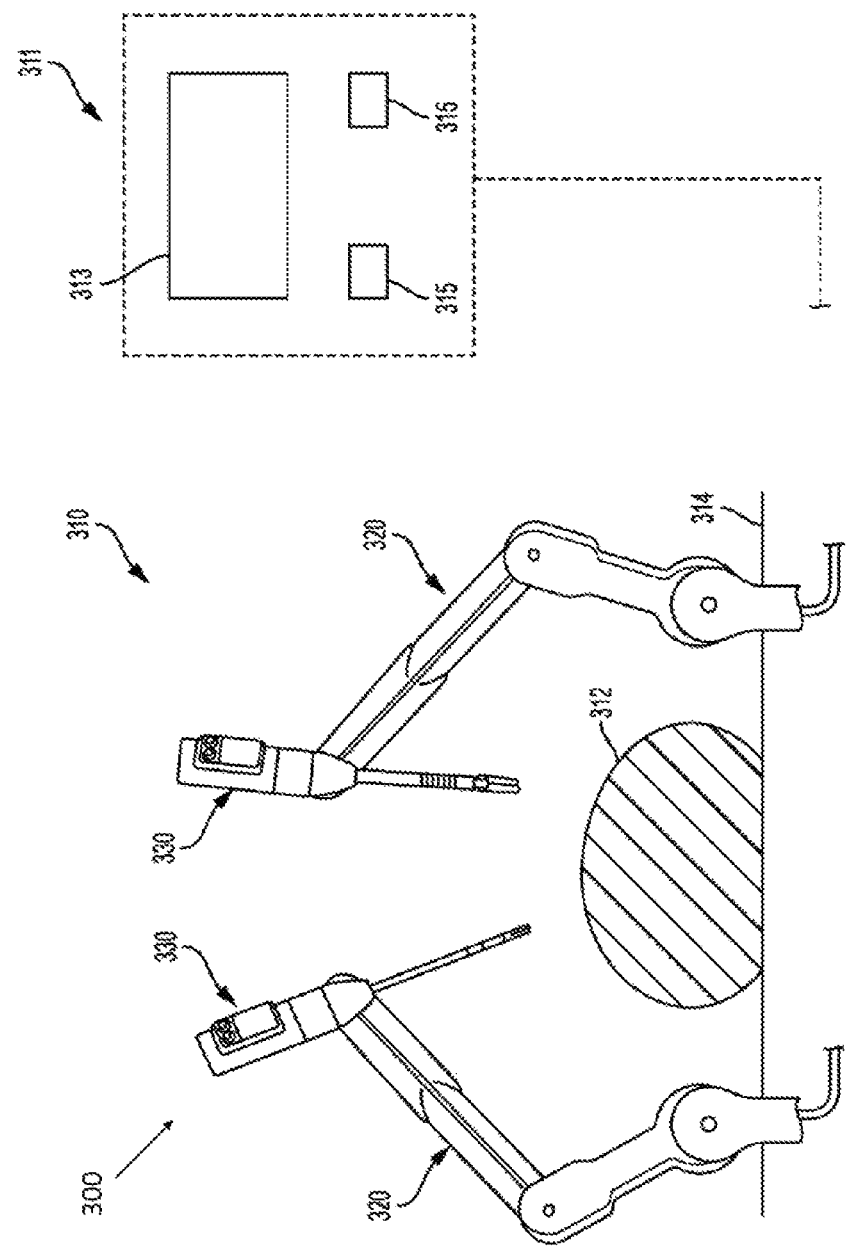
FIG. 1 illustrates a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical tools are provided with multi-axis articulation joints and with the ability to rotate the end effector distal to the joint. A surgical tool can have an elongate shaft with an end effector disposed at a distal end of the elongate shaft. The end effector can have first and second jaws configured to grasp tissue and a sled or cutting element configured to advance through the jaws and cut tissue engaged therebetween. A multi-axis articulation joint can be formed on the shaft or between the shaft and the end effector. The joint can allow articulation of the end effector in multiple directions. For example, the end effector can move left, right, up, down, and any combination thereof. The shaft can include one or more articulation drive members, such as cables, rods, or tubes, that drive articulation of the end effector. One or more of the articulation drive members can be located offset from a central longitudinal axis of the shaft. The articulation joint and the structure of the articulation drive members will allow an articulation force to be transferred through the joint. The joint will also allow the end effector to rotate distal to the multi-axis articulation joint about a longitudinal axis of the elongate shaft. Precise positioning and orientation of the end effector can be achieved by allowing both rotation and multi-axis articulation. A surgeon may enjoy much greater control over the positioning and orientation of the end effector, and thus operations using the end effector may be completed with much greater success.

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication. While the tools and methods are described in connection with a robotic system, the tools and methods can be implemented in hand held devices as well.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
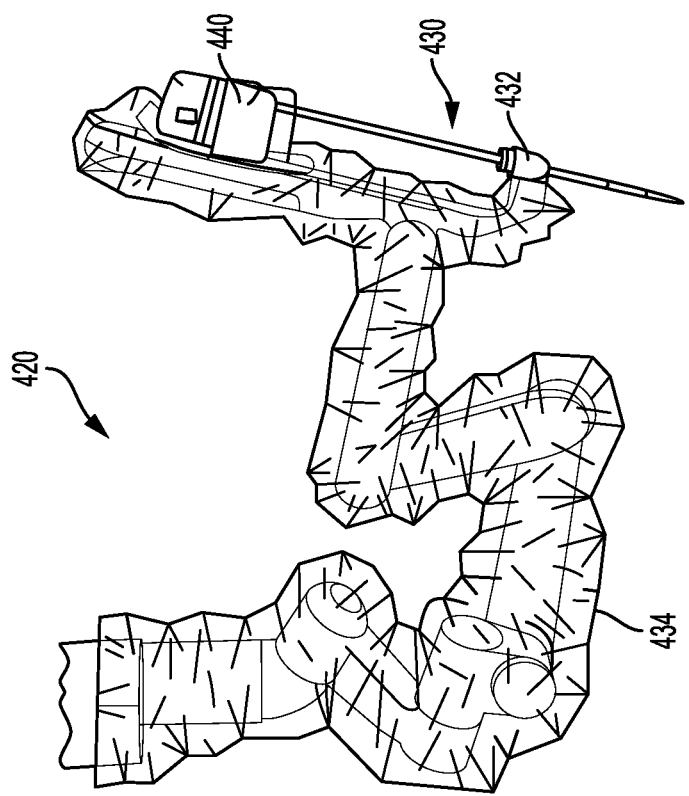
FIG. 2 illustrates an embodiment of a robotic arm of a surgical robotic system with a tool assembly releasably coupled to a tool driver on the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
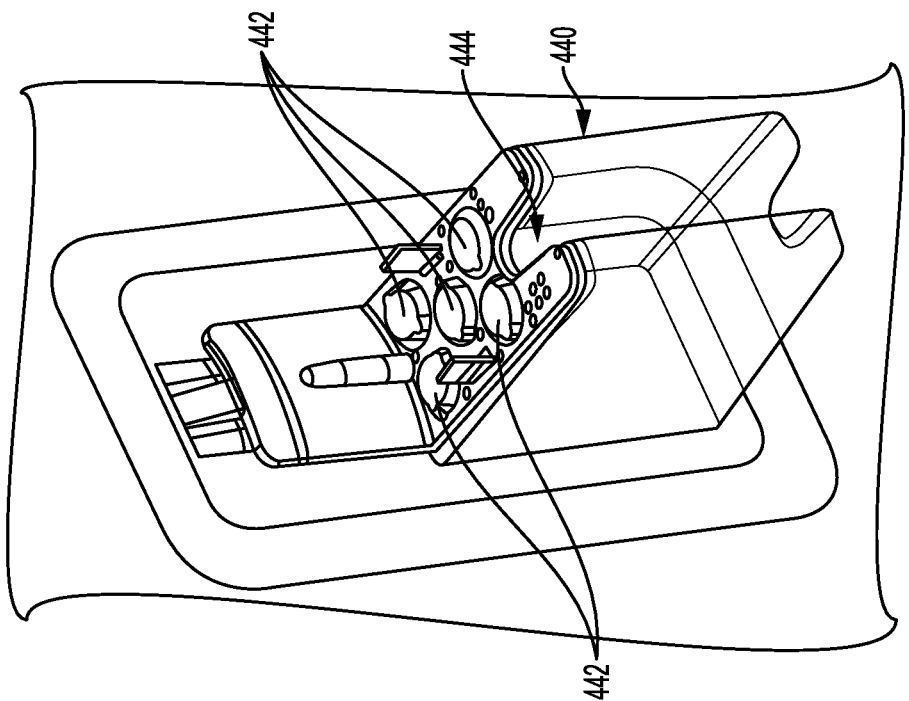
FIG. 3 illustrates a tool driver of the robotic arm of FIG. 2.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
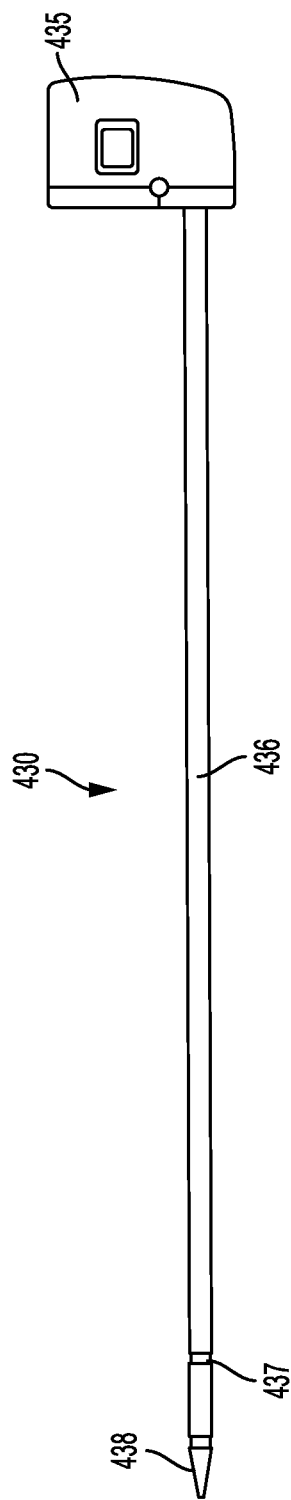
FIG. 4 illustrates the tool assembly of FIG. 2 uncoupled from the robotic arm, the tool assembly including a shaft extending from a tool housing at a proximal end and having an end effector located at a distal end of the shaft.

FIG. 4 illustrates the tool assembly 430 uncoupled from the robotic arm 420. The tool assembly 430 includes a tool housing 435 coupled to a proximal end of a shaft 436 and an end effector 438 coupled to a distal end of the shaft 436. The tool housing 435 can include coupling features that assist with releasably coupling the tool housing 435 to the tool driver 440 of the robotic arm 420. The tool housing 435 can include gears and/or actuators that can be actuated by the one or more motors 442 in the driver 440, as will be described in greater detail below. The gears and/or actuators in the tool housing 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the tool housing 435, or it can be releasably coupled to the tool housing 435 such that the shaft 436 can be interchangeable with other shafts. This can allow a single tool housing 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include a multi-axis articulation joint or wrist 437 that allows a part of the shaft 436 or the end effector 438 to articulate relative to the longitudinal axis A1 of the shaft 436. This can allow for fine movements and various angulation of the end effector 438 relative to the longitudinal axis A1 of the shaft 436. The end effector 438 can have various configurations, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
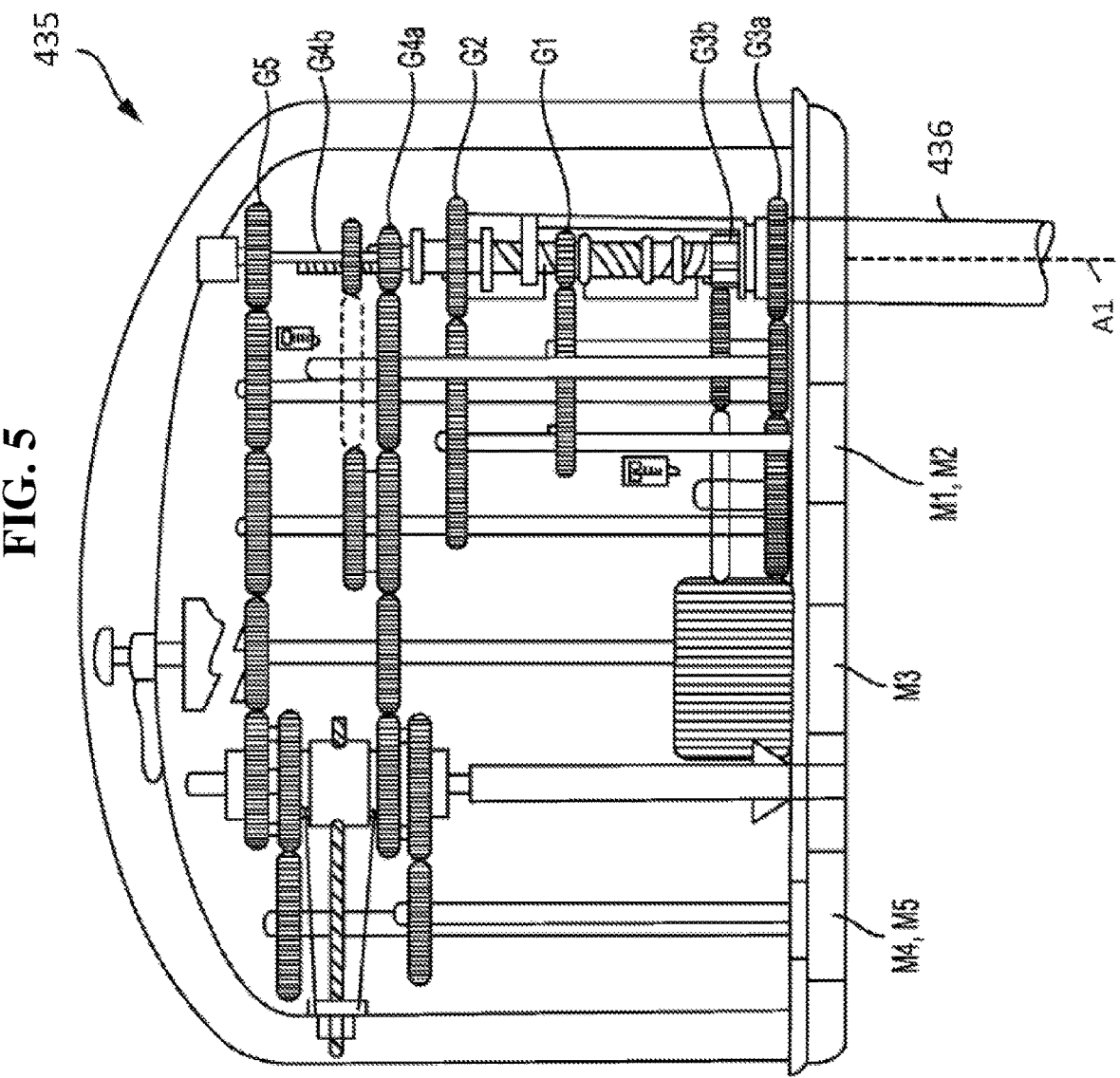
FIG. 5 illustrates the tool housing of the tool assembly of FIG. 4.

FIG. 5 illustrates the tool housing 435 and a proximal end of the shaft 436 extending from the tool housing 435. As shown in FIG. 5, the tool housing 435 includes a plurality of actuation gears and gear shafts that can be either directly or indirectly controlled by any one of the motors 442 associated with the driver 440. For example, as shown in FIG. 5, the tool housing 435 is configured to couple to five motors at the locations indicated by reference numbers M1, M2, M3, M4, and M5. In this embodiment, tool housing 435 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 438 in desired left and right directions. The tool housing 435 also includes a shaft rotation gear G3a that is coupled to the third motor M3 via a series of one or more additional gears and shafts. Actuation of the third motor M3 will thus rotate the shaft rotation gear G3a thereby causing rotation of the shaft 436 of the tool assembly 430. The third motor M3 can also be configured to shift and to couple, via a series of one or more additional gears and shafts, to a head rotation gear G3b, which will cause rotation of the end effector 438 relative to the shaft 436. The tool housing 435 further includes a firm close gear G4a that is coupled to the fourth motor M4 via a series of one or more additional gears and shafts. Actuation of the fourth motor M4 will rotate the firm close gear G4a to cause linear translation of a drive screw to firmly close an upper jaw 450 and/or a lower jaw 452 of the end effector 438. The tool housing 435 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector 438. Finally, the illustrated tool housing 435 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 438, as will be discussed in more detail below.

Figure 6:
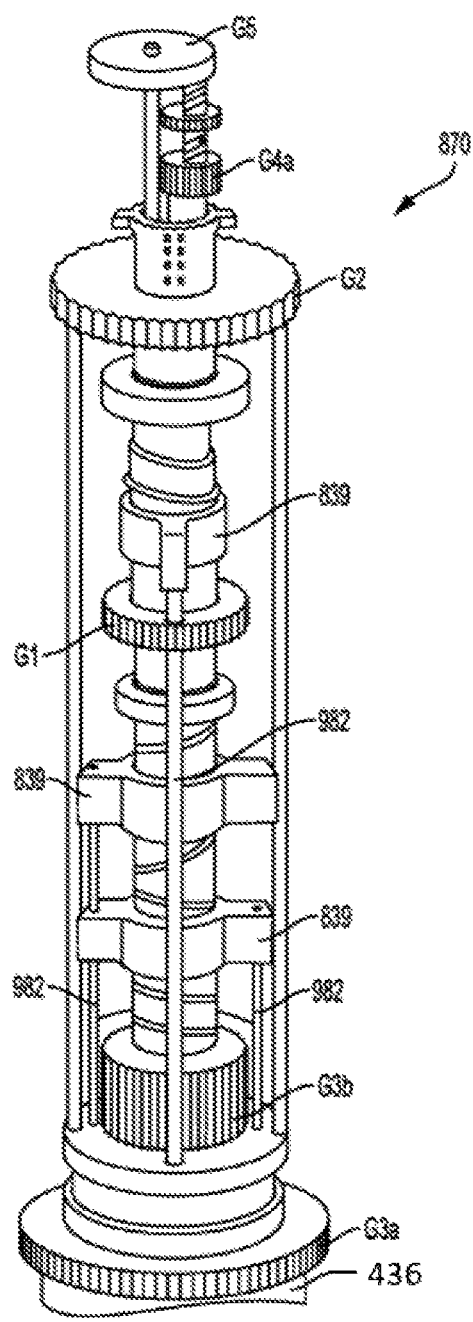
FIG. 6 illustrates an actuation assembly of the tool housing of FIG. 5.

FIG. 6 illustrates the actuation assembly 870 components of the tool housing of FIG. 5. As shown and indicated above, each of the gears G I-G5 is coupled to an actuation shaft that extends from the actuation assembly 870 and along the shaft 436 of the tool assembly 430 for controlling the movements of the end effector.

Figure 7:
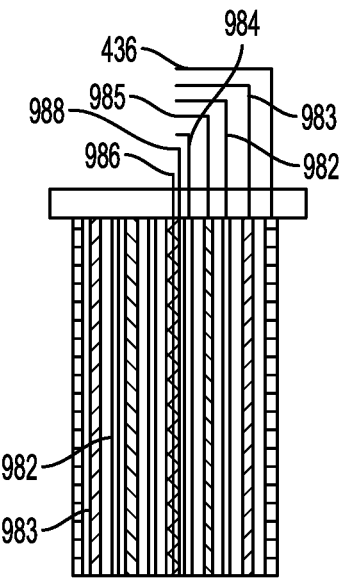
FIG. 7 is a cross-sectional side view of the shaft of the tool assembly of FIG. 4.
Figure 8:
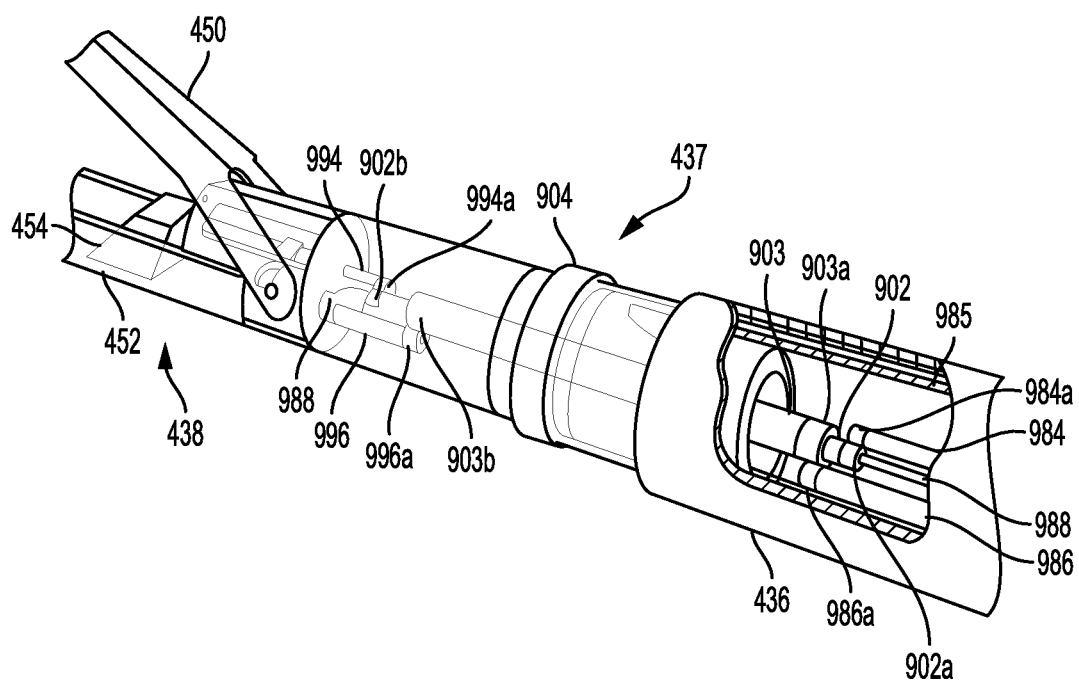
FIG. 8 is a perspective transparent view of the end effector of the tool assembly of FIG. 4.
Figure 9:
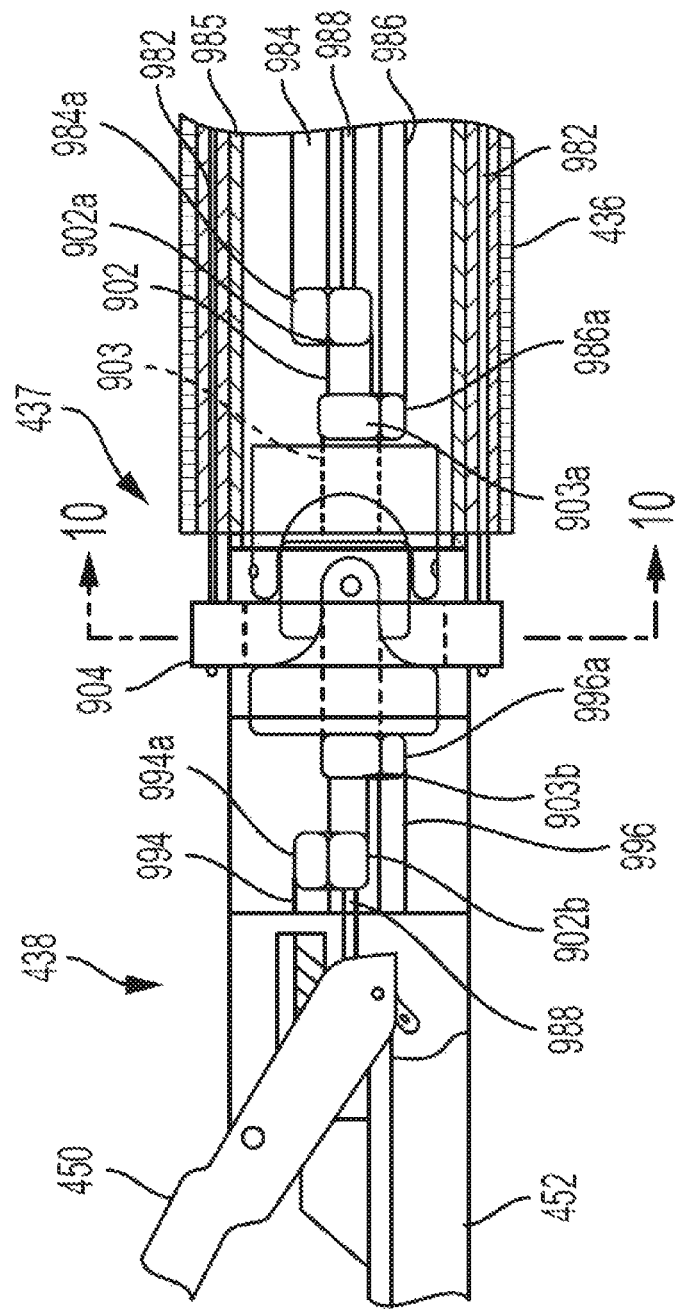
FIG. 9 is a side transparent view of the end effector of FIG. 8.

FIG. 7 illustrates an interior of the elongate shaft 436 that contains actuation shafts positioned proximal from the multi-axis joint 437 located just proximal of the end effector 438. As shown in FIG. 7, the elongate shaft 436 includes two articulation cables 982 and one articulation tube 983 that are spaced around a perimeter of the elongate shaft 436. When actuated (e.g., pushed, pulled), the articulation cables 982 and the articulation tube 983 will cause articulation of the end effector 438 (e.g., movement up, down, left, right, and combinations thereof) relative to the proximal end of the shaft 436. The articulation cables 982 and the articulation tube 983 are connected to the articulation couplers 839, shown in FIG. 6, that are driven proximally and distally when the articulation gears G1, G2 are actuated by the first and second motors M1, M2.

FIG. 7 also illustrates an upper rotary driver 984 that when actuated can cause the pair of jaws of the end effector 438 to firmly close. The upper rotary driver 984 is coupled to the firm close gear G4a shown in FIG. 6 such that rotation of the firm close gear G4a by the motor M4 causes rotation of the rotary driver 984. A lower rotary driver 986 within the shaft 436 can be actuated to cause movement of a sled 454 located in the end effector 438. The lower rotary driver 986 is coupled to the firing gear G5 shown in FIG. 6 and it likewise rotates in response to rotation of the firing gear G5. A linear pull cable 988 extends along the shaft 436 that is coupled to the quick close gear G4b shown in FIG. 6 and that moves linearly in a proximal direction to cause rapid close of the pair of jaws. A rotation shaft 985 within the shaft 436 can cause rotation of the end effector 438 relative to the shaft 436. The rotation shaft 985 is coupled to the head rotation gear G3b shown in FIG. 6 and it likewise rotates within response to rotation of the head rotation gear G3b.

FIGS. 8-11 illustrate the end effector 438 with the multi-axis articulation joint or wrist 437 that allows the end effector 438 to articulate relative to the longitudinal axis of the shaft 436 and that allows rotation of the end effector 438 about the longitudinal axis of the elongate shaft 436 independent of any actuation of the end effector 438, allowing a user to perform fine movements and various angulations of the end effector 438 relative to the longitudinal axis of the shaft 436 and thus allowing greater control and precision during operations requiring the end effector 438.

Figure 10:
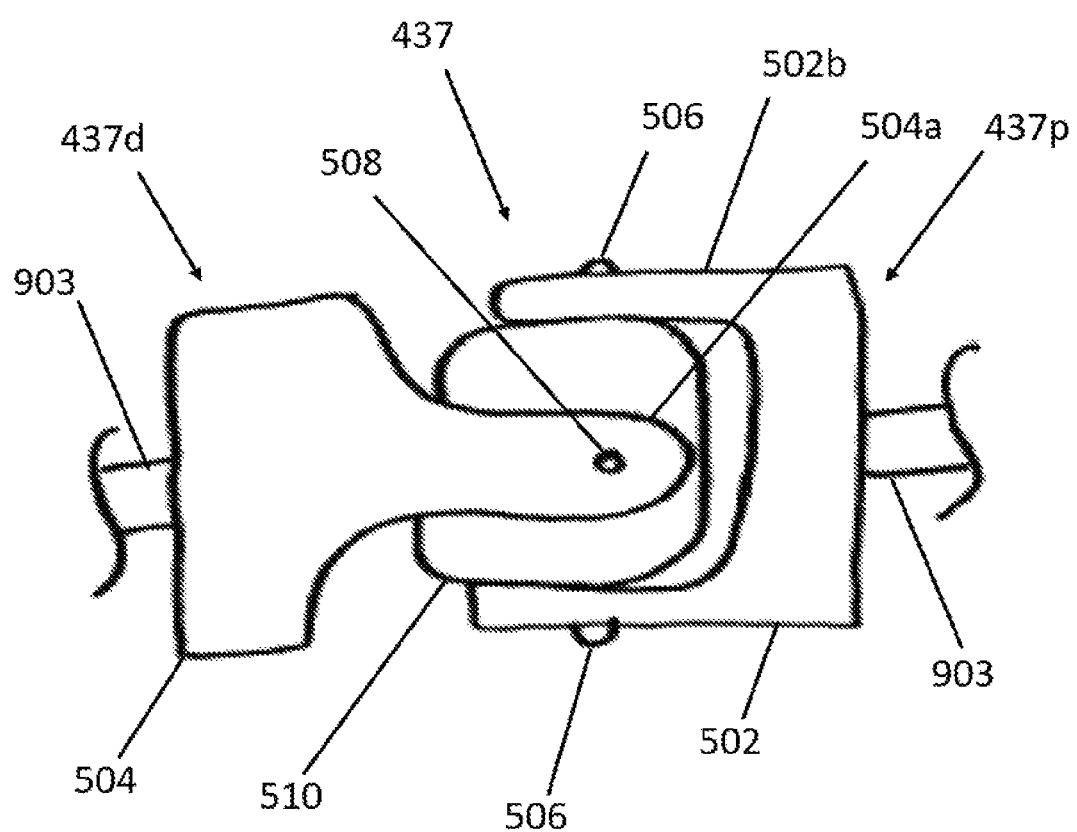
FIG. 10 is a side view of the articulation joint of FIG. 8.

The illustrated multi-axis joint 437 is a flexible universal joint coupling the end effector 438 to the distal end of the elongate shaft 436. As illustrated in FIG. 10, the joint 437 includes a first u-shaped arm 502 and a second u-shaped arm 504. The two arms 502, 504 are pivotably coupled together by first and second pivot pins 506, 508 that pass through a middle bracket 510. Arm 502 can pivot about a longitudinal axis of the first pivot pin 506 and arm 504 can pivot about a longitudinal axis of the second pivot pin 508. The first pivot pin 506 extends from one edge 502a of the first u-shaped arm 502, through the middle bracket 510, and terminates on an opposite edge 502b of the first u-shaped arm 502. The second pivot pin 508 extends from one edge 504a of the second u-shaped arm 504, through the middle bracket 510, and terminates on an opposite edge (hidden by the edge 504a in FIG. 10) of the second u-shaped arm 504.

The upper rotary driver 984, the lower rotary driver 986, and the linear pull cable 988 extend through the elongate shaft 436 in a non-concentric manner. The upper rotary driver 984 and the lower rotary driver 986 are offset from the central longitudinal axis of the shaft 436, while the linear pull cable 988 is aligned along central longitudinal axis of the shaft 436. The upper rotary driver 984 and the lower rotary driver 986 are coupled to torque transmission tubing 902, 903 just proximal to the multi-axis joint 437, with the upper rotary driver 984 coupling to the torque transmission tubing 902 and the lower rotary driver 986 coupling to the torque transmission tubing 903. The upper rotary driver 984 terminates distally in a gear 984a having teeth that engage teeth on a gear 902a on a proximal end of the torque transmission tubing 902. Rotation of the upper rotary driver 984 thus causes rotation of the torque transmission tubing 902 through engagement of the teeth. The lower rotary driver 986 terminates distally in a gear 986a having teeth that engage teeth on a gear 903a on a proximal end of the torque transmission tubing 903. Rotation of the lower rotary driver 986 thus causes rotation of the torque transmission tubing 903 through engagement of the teeth.

While the upper rotary driver 984 and the lower rotary driver 986 are not concentric and are offset from the central longitudinal axis of the shaft 436, the two torque transmission tubes 902, 903 are concentric with each other and with the linear pull cable 988. The linear pull cable 988 extends inside of torque transmission tubing 902, and torque transmission tubing 902 extends inside of torque transmission tubing 903. All three extend through the central bracket 510 and generally extend through a center of the joint 437 from a proximal side 437p of the joint 437 to a distal side 437d of the joint 437. The torque transmission tubing 902, 903 and the linear pull cable 988 are flexible, allowing the joint 437 to pivot even while extending through its center.

Figure 11:
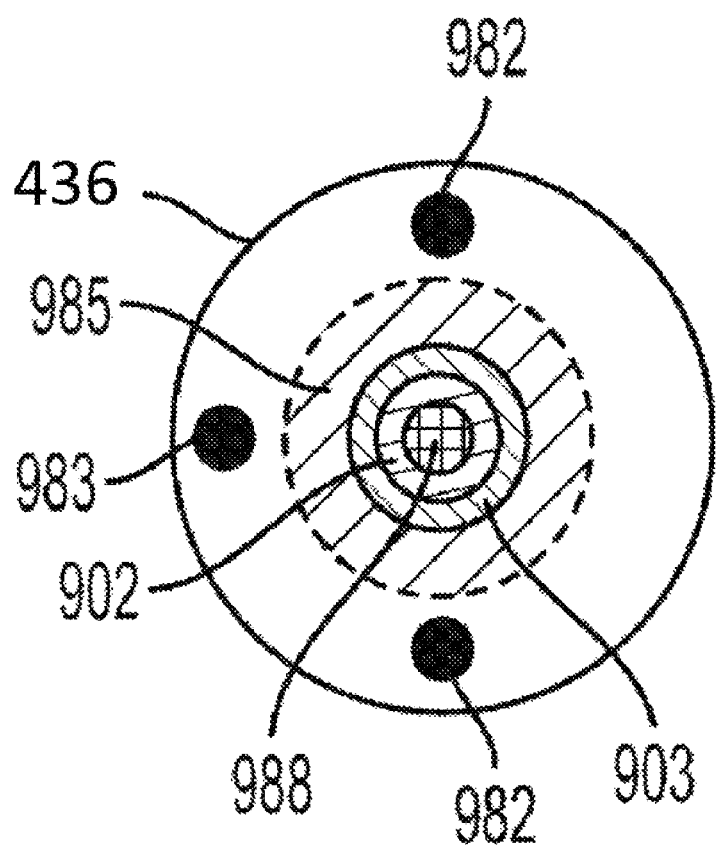
FIG. 11 is a cross-sectional view of the end effector of FIG. 9 taken along a line A-A.

As illustrated in FIG. 11, on the distal side 437d of the joint 437, the torque transmission tubing 902 couples to an upper rotary driver 994. Torque transmission tubing 902 terminates distally in a gear 902b having teeth that engage teeth on a gear 994a on a proximal end of the upper rotary driver 994. Rotation of the torque transmission tubing 902 thus causes rotation of the upper rotary driver 994 through engagement of the teeth. Torque transmission tubing 903 couples to a lower rotary driver 996. The lower torque transmission tubing 903 terminates distally in a gear 903b having teeth that engage teeth on a gear 996a on a proximal end of the lower rotary driver 996. Rotation of the low torque transmission tubing 903 thus causes rotation of the lower rotary driver 996 through engagement of the teeth. The linear pull cable 988 couples to one of the upper jaw 450 or the lower jaw 452 on the end effector, and the linear pull cable 988 can be pulled proximally to cause quick close of the jaws. Actuation of firing, quick close, and firm close functionality of the end effector 438 is thus effectively transferred across the joint 437 to the end effector 438.

Regarding articulation and rotation, the two articulation cables 982 and the articulation tube 983 extend through the elongate shaft 436 and terminate distally at a rotation coupling 904. Articulation tube 983 is configured to prevent rotation of the rotation coupling 904, thus allowing the end effector 438 to rotate independent of and relative to the rotation coupling 904.

The rotation shaft 985 extends distally along the elongate shaft 436 and couples at a distal end to a proximal end 437p of the joint 437. The rotation shaft 985 is configured to rotate about the longitudinal axis of the elongate shaft 436, to thereby rotate the joint 437 about the longitudinal axis of the elongate shaft 436. The joint 437 is coupled on a distal end 437d to the end effector 438, thereby causing corresponding rotation of the end effector 438 when the joint 437 rotates. The end effector 438 is rotated independent of any articulation of the joint 437 and independent of and relative to the rotation coupling 904. The rotation shaft 985 thus allows the end effector 438 to rotate about the longitudinal axis of the elongate shaft 436 without preventing or interfering with articulation of the joint 437 or functionality of the end effector 438, thus providing complete control over both the functionality and the orientation of the end effector during minimally invasive surgery.

There are several general aspects that apply to the various descriptions herein. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Through manipulation of a control system such as the control system 315 discussed above, a user can control one or more parts of a surgical system incorporating the robotic arm 420 and the tool assembly 430 discussed above. For example, a user can control the robotic arm 420 that supports and moves the associated tool assembly 430 along one or more mechanical degrees of freedom. Input from the user can control the tool driver 440, which can assist with controlling features associated with the tool assembly 430. During a minimally-invasive surgery, the user can manipulate the robotic arm 420 to introduce the tool assembly 430 through the entry guide 432 (e.g., a cannula mount or cannula). The user can thus direct insertion of the shaft 436 of the tool assembly 430 and the end effector 438 through the entry guide 430 and into the body of a patient, and the user can actuate the motors M1, M2, M3, M4, and M5 to interact with the tool housing 435. Through interaction between the user and the control system, the tool assembly 430 can be oriented and positioned such that tissue is between the first and second jaws 450, 452 of the end effector 438. Articulation can be caused by a user manipulating the surgical system to cause movement of the articulation cables 982 and the articulation tube 983, causing actuation of the multi-axis articulation joint 437 and consequently the end effector 438. Independently of actuation of the end effector 438 about the multi-axis articulation joint 437 by the articulation cables 982 and the articulation tube 983, the end effector 438 can also be rotated by a user through the control system by actuation of the rotation shaft 985, which couples to the proximal end 900p of the universal joint 900 and rotates about the longitudinal axis of the elongate shaft 436 (and consequently causes rotation of the universal joint 900 and the end effector 438).

When tissue has been positioned between the jaws 450, 452, a user can actuate the control system to cause rotation of the upper rotary driver 984, rotation of the lower rotary driver 986, and/or linear movement of the linear pull cable 988. The jaws 450, 452 can close on tissue positioned therebetween and/or the sled 454 can be actuated to advance through the end effector 438, thereby firing staples and cutting tissue engaged between the jaws 450, 452. After firing and/or grasping, the control system can be used to open the jaws and retract and/or reposition the end effector 438.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
   an elongate shaft;
   an end effector coupled to a distal end of the elongate shaft, the end effector including first and second jaws movable between an open position in which the first and second jaws are spaced apart from one another, and a closed position in which the first and second jaws are configured to engage tissue therebetween;
   a joint coupled between the elongate shaft and the end effector, the joint being configured to allow multi-axis articulation of the end effector relative to the elongate shaft;
   a plurality of articulation members extending distally through the elongate shaft, at least one of the plurality of articulation members being offset from a central longitudinal axis of the elongate shaft;
   a first rotary driver having a first flexible torque transmission tube, the first rotary driver extending distally through the elongate shaft, the first rotary driver being operatively connected to the end effector such that rotation of the first rotary driver is configured to move the first and second jaws between the open and closed positions, and the first flexible torque transmission tube extending through the joint; and
   a linear pull cable extending distally through the elongate shaft and the joint, the linear pull cable being at least partially disposed within the first flexible torque transmission tube.

2. The surgical tool of claim 1, wherein the first flexible torque transmission tube extends through a center of the joint.

3. The surgical tool of claim 1, further comprising a second rotary driver coupled to the end effector such that rotation of the second rotary driver is configured to advance a cutting element through the end effector.

4. The surgical tool of claim 1, wherein the plurality of articulation members are configured to translate longitudinally along the elongate shaft to articulate the end effector.

5. The surgical tool of claim 4, wherein the plurality of articulation members comprises a first articulation cable, a second articulation cable, and an articulation tube.

6. The surgical tool of claim 1, further comprising a rotation shaft extending through the elongate shaft and operatively connected to the joint such that rotation of the rotation shaft causes rotation of the joint and corresponding rotation of the end effector relative to the elongate shaft.

7. The surgical tool of claim 1, wherein a proximal end of the elongate shaft is coupled to a housing that is configured to couple to a plurality of motors on a tool driver of a surgical system.

8. The surgical tool of claim 1, wherein the first rotary driver includes a proximal gear positioned proximal of the joint, and a distal gear positioned distal of the joint, the proximal and distal gears being configured to translate a rotational force from the first rotary driver across the joint.

9. The surgical tool of claim 1, wherein linear actuation of the linear pull cable is configured to move the first and second jaws between the open and closed positions.

10. The surgical tool of claim 1, wherein the linear pull cable is coaxial with the first flexible torque transmission tube through the joint.

11. A robotic tool, comprising:
    a housing having a plurality of gear assemblies, each of the plurality of gear assemblies being configured to couple to at least one motor on a tool driver of a surgical robot;
    an elongate shaft extending distally from the housing;
    an end effector having first and second jaws pivotably coupled to a distal end of the elongate shaft, the end effector being rotatable about a longitudinal axis thereof;
    a multi-axis articulation joint coupled between the elongate shaft and the end effector and configured to allow multi-axis articulation of the end effector; and
    a plurality of rotatory drive actuators extending through the elongate shaft and configured to actuate at least closing of the first and second jaws, the plurality of rotary drive actuators including a first flexible torque transmission tubing and a second flexible torque transmission tubing coaxial with one another such that the first flexible torque transmission tubing is disposed within the second flexible torque transmission tubing, the first and second torque transmission tubing extending through a center of the articulation joint.

12. The robotic tool of claim 11, wherein the plurality of rotatory drive actuators comprise non-concentric actuators.

13. The robotic tool of claim 11, further comprising a sled disposed within the end effector and configured to advance distally through at least one of the first and second jaws to eject at least one staple into tissue engaged between the first and second jaws, wherein at least one of the plurality of rotatory drive actuators is configured to actuate advancement of the sled.

14. The robotic tool of claim 13, wherein the plurality of rotatory drive actuators comprise a first flexible torque transmission tubing and a second flexible torque transmission tubing concentric with one another and extending through a center of the articulation joint, the first flexible torque transmission tubing being configured to actuate closing of the first and second jaws, the second flexible torque transmission tubing being configured to actuate advancement of the sled.

15. The robotic tool of claim 11, further comprising a first articulation cable, a second articulation cable, and an articulation tube that extend distally through the elongate shaft and that are coupled to the articulation joint.

16. A surgical method, comprising:
actuating a first motor on a tool driver of a surgical robot to cause an actuation shaft extending through a shaft of a tool coupled to the tool driver to rotate and thereby cause opposed jaws on an end effector of the tool to close, the actuation shaft extending offset from a central longitudinal axis of the shaft, and the rotary force being transferred across an articulation joint that allows multi-axial articulation of the end effector through rotation of at least first and second torque transmission tubes extending coaxially with one another through the articulation joint such that one of the first or second torque transmission tubes is disposed within the other; and actuating a second motor on the tool driver to rotate a rotation actuation shaft extending through the shaft of the tool to thereby cause rotation of the end effector relative to the shaft and distal of the articulation joint.

17. The surgical method of claim 16, further comprising actuating an additional motor on the tool driver to articulate at least one articulation member extending through the shaft of the tool, which thereby causes articulation of the end effector relative to the shaft.

18. The surgical method of claim 16, further comprising actuating an additional motor on the tool driver to cause a second actuation shaft extending through the shaft to rotate and thereby cause a cutting element disposed within the opposed jaws to advance to cut tissue grasped between the opposed jaws, the actuation shaft extending offset from the central longitudinal axis of the shaft.

19. The surgical method of claim 16, further comprising actuating an additional motor on the tool driver to cause at least one articulation cable to translate longitudinally along the shaft and thereby cause the end effector to articulate about the articulation joint.

* * * * *